United States Patent [19]

Asinger et al.

[11] 3,947,464
[45] Mar. 30, 1976

[54] SALTS OF PHENYLPROPANOLAMINE WITH THIAZOLIDINE CARBOXYLIC ACIDS

[75] Inventors: Friedrich Asinger, Rott; Heribert Offermanns, Grossauheim, both of Germany

[73] Assignee: Deutsche Gold- und Silber-Scheideanstalt vormals Roessler, Germany

[22] Filed: Nov. 27, 1973

[21] Appl. No.: 419,448

Related U.S. Application Data

[63] Continuation-in-part of Ser. No. 276,236, July 28, 1972, abandoned.

[30] Foreign Application Priority Data

Nov. 29, 1972  Germany.............................. 2258410

[52] U.S. Cl.......................................... 260/306.7 C
[51] Int. Cl.²...................................... C07D 277/04
[58] Field of Search.................... 260/306.7 C, 534 S

[56] References Cited
UNITED STATES PATENTS 2,450,784   10/1948   Duffin et al.................. 260/306.7 C
3,290,325   12/1966   Betrand........................ 260/306.7 C

*Primary Examiner*—Richard J. Gallagher
*Assistant Examiner*—Anne Marie T. Tighe
*Attorney, Agent, or Firm*—Cushman, Darby & Cushman

[57]     ABSTRACT

The d,l-phenylpropanolamine racemate is split with optically active thiazolidine-4-carboxylic acids of the formula:

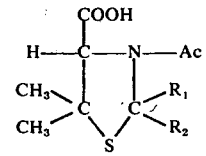

where $R_1$ $R_2$ are hydrogen, alkyl of 1 to 8 carbon atoms, cycloalkyl, aryl or alkylene of at least 2 carbon atoms or $R_1$ and $R_2$ together form a ring of alkyl or alkylene with 4 to 12 carbon atoms and AC is acyl, especially benzoyl, tosyl, nitrophenylsulfenyl, acetyl or preferably formyl.

7 Claims, No Drawings

SALTS OF PHENYLPROPANOLAMINE WITH THIAZOLIDINE CARBOXYLIC ACIDS

The present application is a continuation-in-part of application Ser. No. 276,236, filed July 28, 1972, now abandoned, the entire disclosure of which is hereby incorporated by reference.

l-Phenylpropanolamine is an important starting material for the synthesis of medicines. It is recovered from molasses by fermentation processes. However, it is also known to produce l-phenylpropanolamine by racemate splitting of d,l-phenylpropanolamine with the help of optically active tartaric acid (Liebigs Annalen der Chemie, Vol. 470, pages 157–182). This process is not very satisfactory since the solubility differences of the diastereomer salts are too slight as a result of which multiple recrystallizations of the salts are necessary. As a result the yields are very unsatisfactory.

It has now been found that there can be obtained optically active phenylpropanolamine (norephedrine) and especially l-phenylpropanolamine (l-norephedrine) in high yields and in high purity by splitting the racemate of d,l-phenylpropanolamine (d,l-norephedrine) with optically active acids if there is used as the optically active acid an optically active thiazolidine-4-carboxylic acid of the general formula:

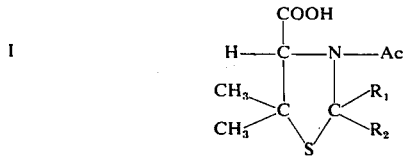

in which $R_1$ and $R_2$ are the same or different and are hydrogen, alkyl of 1 to 8 carbon atoms, cycloalkyl, aryl, or alkylene of at least 2 carbon atoms, e.g. 4 to 5 carbon atoms, i.e. carbocyclic aryl, or $R_1$ and $R_2$ together form a ring of alkyl or alkylene with 4 to 12 carbon atoms and Ac is an acyl group, especially benzoyl, tosyl, nitrophenylsulfenyl, lower alkanoyl, e.g. acetyl or preferably formyl.

The preferred optically active acid is 3-formyl-2,2,5,5-tetramethyl-thiazolidine-4-carboxylic acid. Correspondingly to recover l-phenylpropanolamine there is employed D-3-formyl-2,2,5,5-tetramethyl-thiazolidine-4-carboxylic acid.

Other optically active acids which can be used and which are within formula I include D-3-acetyl-2,2,5,5-tetramethyl-thiazolidine-4-carboxylic acid, L-3-acetyl-2,2,5,5-tetramethyl-thiazolidine-4-carboxylic acid, D-3-propionyl-2,2,5,5-tetramethyl-thiazolidine-4-carboxylic acid, D-3-benzoyl-2,2,5,5-tetramethyl-thiazolidine-4-carboxylic acid, L-3-benzoyl-2,2,5,5-tetramethyl-thiazolidine-4-carboxylic acid, D-3-p-toluenesulfonyl-2,2,5,5-tetramethyl-thiazolidine-4-carboxylic acid, L-3-tosyl-2,2,5,5-tetramethyl-thiazolidine-4-carboxylic acid, D-3-p-nitrophenylsulfenyl-2,2,5,5-tetramethyl-thiazolidine-4-carboxylic acid, D-3-formyl-2,2-diethyl-5,5-dimethyl-thiazolidine-4-carboxylic acid, L-3-formyl-2,2-diethyl-5,5-dimethyl-thiazolidine-4-carboxylic acid, D-N-formyl-2,2-pentamethylene-5,5-dimethyl-thiazolidine-4-carboxylic acid, D-3-formyl-2,2-dioctyl-5,5-dimethyl-thiazolidine-4-carboxylic acid, L-N-formyl-2,2-pentamethylene-5,5-dimethyl-thiazolidine-4-carboxylic acid, D-3-formyl-2,2-dibutyl-5,5-dimethyl-thiazolidine-4-carboxylic acid, L-3-formyl-2,2-dicyclohexyl-5,5-dimethyl-thiazolidine-4-carboxylic acid, D-N-formyl-2,2-tetramethylene-5,5-dimethyl-thiazolidine-4-carboxylic acid, D-3-formyl-2,2-diphenyl-5,5-dimethyl-thiazolidine-4-carboxylic acid, L-3-formyl-2,2-di o-tolyl-5,5-dimethyl-thiazolidine-4-carboxylic acid, D-3-acetyl-2,2-dihexyl-5,5-dimethyl-thiazolidine-4-carboxylic acid, D-3-tosyl-2-phenyl-2-p-tolyl-5,5-dimethyl-thiazolidine-4-carboxylic acid.

As organic solvents for the reaction there can be used alcohols, halogenated aliphatic hydrocarbon, ethers, ketones, esters, aromatic hydrocarbons, etc. There are preferably used benzene, toluene, isopropanol, dioxane and lower carboxylic acid esters, e.g. ethyl acetate.

Specific examples of additionally suitable solvents include methanol, ethanol, butanol, isooctyl alcohol, isodecyl alcohol, dodecyl alcohol, chloroform, carbon tetrachloride, dichloroethylene, 1,1,2,2-tetrachloroethane, dibromoethylene, acetone, methyl ethyl ketone, methyl butyl ketone, diethyl ketone, diethyl ether, dimethyl ether, dipropyl ether, dibutyl ether, ethyl formate, ethyl propionate, methyl formate, ethyl formate, ethyl propionate, ethyl butyrate, propyl acetate, ethyl propionate.

In carrying out the process of the invention suitably d,l-phenyl-propanolamine is dissolved in water or more preferably in an organic solvent such as those set forth above and this solution, in a given case with heating, treated with the optically active thiazolidine-4-carboxylic acid of formula I, in a given case dissolved in an organic solvent, e.g. any of the organic solvents set forth above. Thereupon frequently immediately, on occasion, however, only after long standing, in a given case at low temperatures and after inoculation (seeding), the difficultly soluble salt of the optically active amine and the optically active thiazolidine-4-carboxylic acid of general formula I precipitates. The diastereoisomeric salt, the optical antipode, remaining optically active adjuvant acid or racemic mixture or mixtures thereof remain in the mother liquor.

However, the reverse can occur and the solution of the optically active thiazolidine-4-carboxylic acid of general formula I in water or more preferably in an organic solvent be treated with the racemic mixture of phenylpropanolamine which preferably is dissolved in an organic solvent, e.g. any of those set forth supra.

According to the process of the invention there can be used 0.1 to 3 moles, preferably 0.5 to 1.1 moles of the optically active thiazolidine-4-carboxylic acid of general formula I per mole of racemate. In all ranges the more difficultly soluble salt of the optically active phenylpropanolamine and optically active thiazolidine-4-carbozylic acid precipitates out. This precipitation is nearly quantitative if the amounts of reactants are kept nearly stoichiometric. By the use of less than 0.5 mole of the thiazolidine-4-carboxylic acid per mole of phenyl-propanolamine racemate there remains in the mother liquor the racemate and optical antipode. If there is used per mole of racemate 0.5 to < 1 mole of optically active thiazolidine-4-carboxylic acid, the mother liquor contains besides the optical antipode diastereoisomeric salt. If there is added per mole of racemate more than 1 mole of thiazolidine-4-carboxylic acid, there remains in the mother liquor in addition to the diastereoisomeric salt optically active thiazolidine-4-carboxylic acid.

The salt of the optically active phenylpropanolamine and the optically active thiazolidine-4-carboxylic acid of formula I resulting from the conversion can be recovered in pure form in known manner, because of its very favorable solubility differentiations, for example by filtration, evaporation of the mother liquor, purification by recrystallization. The splitting of the salt can be carried out in known manner by treating with preferably aqueous mineral acids, for example hydrochloric acid, hydrobromic acid, sulfuric acid, phosphoric acid, whereby the mineral acid salt of the optically active base is formed and the optically active thiazolidine-4-carboxylic acid can be recovered in high yields.

If there are used non stoichiometric amounts of the optically active thiazolidine-4-carboxylic acid, it is possible to separate the difficultly soluble salt of the optically active amine and optically active thiazolidine-4-carboxylic acid from the diastereoisomeric salt, the racemic amine mixture and the optical antipode or their mixture because of the favorable solubility differentiation likewise in manner known in itself.

The process of the invention is especially suitable for the recovery of l-phenylpropanolamine using D-thiazolidine-4-carboxylic acids of formula I. The optically pure thiazolidine-4-carboxylic acids can be recovered from the racemic acid mixture in known manner, for example using brucine (in the manner described in Duffin U.S. Pat. No. 2,450,784 or British patent 585,413), preferably, however, using for example l-phenylpropanolamine produced by fermentation.

The thiazolidine-4-carboxylic acid of formula I can be produced for example by the process described in Belgian patent 738,520.

Unless otherwise indicated all parts and percentages are by weight.

EXAMPLE 1

21.7 gram (0.1 mole) of D-3-formyl-2,2,5,5-tetramethyl-thiazolidine-4-carboxylic acid were dissolved in 150 ml of ethyl acetate with heating and mixed at about 70°C. with a solution of 15.1 grams (0.1 mole) of d,l-phenylpropanolamine in 45 ml. of ethyl acetate. After a short time the salt of l-phenylpropanolamine and D-3-formyl-2,2,5,5-tetramethyl-thiazolidine-4-carboxylic acid precipitated out. After 30 minutes heating at reflux and cooling to room temperature the product was filtered off with strong suction and washed with 20 ml of ethyl acetate. After drying at 45°C. under reduced pressure there were obtained 17.5 grams (95%) of the salt melting at 198°–199°C.; $[\alpha]_D^{20} + 36°$. The salt was treated at room temperature with 80 ml of dilute hydrochloric acid (1:10). There were obtained after filtering with suction 9.7 grams (90%) of D-3-formyl-2,2,5,5-tetramethyl-thiazolidine-4-carboxylic acid with $[\alpha]_D^{20} + 51°$ as the constituent insoluble in the dilute hydrochloric acid. From the mother liquor there were obtained 9.2 grams (98%) of l-phenylpropanolamine.HCl which after a single recrystallization from isopropyl alcohol melted at 165°C.; $[\alpha]_D^{20} - 36°$. After evaporation of the mother liquor of racemic splitting to dryness there were obtained 18 grams (96%) of the salt of d-phenylpropanolamine and D-3-formyl-2,2,5,5-tetramethyl-thiazolidine-4-carboxylic acid. By splitting of the salt which was carried out in a manner analogous to that described, there was obtained 6.2 grams (66.5%) of d-phenylpropanolamine.HCl, that after recrystallization from isopropyl alcohol melted at 158°C.; $[\alpha]_D^{20} + 35.4°$.

EXAMPLE 2

21.7 grams (0.1 mole) of D-3-formyl-2,2,5,5-tetramethyl-thiazolidine-4-carboxylic acid were dissolved in 150 ml of ethyl acetate with heating to 50°C. and mixed with a solution of 30.2 grams (0.2 mole) of d,l-phenylpropanolamine in 150 ml of ethyl acetate at this temperature. After heating for 20 minutes under reflux and subsequently cooling to room temperature the product was filtered off with strong suction and subsequently washed with 30 ml of ethyl acetate. There were obtained 34.7 grams (95%) of the salt of l-phenylpropanolamine and D-3-formyl-2,2,5,5-tetramethyl-thiazolidine-4-carboxylic acid melting at 193°C.; $[\alpha]_D^{20} + 35.8°$.

The splitting of the salt which was carried out as described in example 1 resulted in 15.4 grams (71%) of D-3-formyl-2,2,5,5-tetramethyl-thiazolidine-4-carboxylic acid as well as 15 grams (82%) of l-phenylpropanolamine.HCl having the melting point 165°C.; $[\alpha]_D^{20} - 32°$. From the mother liquor of the racemate splitting there were obtained after evaporation to dryness and treatment with isopropanolic HCl 12 grams (65%) of d-phenylpropanolamine. HCl having $[\alpha]_D^{20} + 35.5°$.

EXAMPLE 3

60.4 grams (0.4 mole) of d,l-phenylpropanolamine were dissolved in 500 ml of ethyl acetate with heating. To this solution there were added dropwise inside 20 minutes a solution of 43.4 grams (0.2 mole) of L-3-formyl-2,2,5,5-tetramethyl-thiazolidine-4-carboxylic acid in 100 ml of ethyl acetate. After 30 minutes heating under reflux and cooling to room temperature the product was filtered off with strong suction and there were obtained 70 grams (95%) of the salt of d-phenylpropanolamine and L-3-formyl-2,2,5,5-tetramethyl-thiazolidine-4-carboxylic acid that after a single recrystallization from isopropanol melted at 203°C.; $[\alpha]_D^{20} - 34.3°$.

61 grams of this salt were split in a manner analogous to that described in example 1. There were obtained 33 grams of L-3-formyl-2,2,5,5-tetramethyl-thiazolidine-4-carboxylic acid melting at 179° – 180°C.; $[\alpha]_D^{20} - 54.4°$ as well as 26.5 grams of d-phenylpropanolamine.HCl melting point 173°C.; $[\alpha]_D^{20} + 33°$. From the mother liquor of the racemate splitting by evaporation to dryness and treatment with isopropanolic HCl there were obtained 28 grams (77%) of l-phenylpropanolamine.HCl, melting point 179°C.; $[\alpha]_D^{20} - 31.4°$.

EXAMPLE 4

The procedure of example 1 was employed except that acetone was used as the solvent for the splitting of the racemate. There was obtained the salt of l-phenylpropanolamine and D-3-formyl-2,2,5,5-tetramethyl-thiazolidine-4-carboxylic acid in a yield of 84%, melting point 210°C.; $[\alpha]_D^{20} + 32.8°$.

EXAMPLE 5

The procedure of example 1 was employed except that isopropyl alcohol was used as the solvent. There was obtained the salt of l-phenylpropanolamine and D-3-formyl-2,2,5,5-tetramethyl-thiazolidine-4-carboxylic acid in a yield of 81%. Melting point 201°C.; $[\alpha]_D^{20} + 34.1°$.

EXAMPLE 6

The procedure of example 1 was employed except that dioxane was used as the solvent. There was obtained the salt of l-phenylpropanolamine and D-3-formyl-2,2,5,5-tetramethylthiazolidine-4-carboxylic aicd in a yield of 72%. Melting point 197°C.; $[\alpha]_D^{20} + 32.8°$.

EXAMPLE 7

43.5 grams (0.2 mole) of D,L-3-formyl-2,2,5,5-tetramethyl-thiazolidine-4-carboxylic acid were dissolved in 300 ml of ethyl acetate with heating and mixed with a solution of 33.3 grams (0.22 mole) of l-phenylpropanolamine (recovered from molasses by fermentation) dissolved in 100 ml of ethyl acetate. After heating for 30 minutes under reflux the mixture was cooled, filtered off with strong suction and subsequently washed with 100 ml of ethyl acetate. There were obtained 34.6 grams (94%) of the salt of l-phenyl-propanolamine and D-3-formyl-2,2,5,5-tetramethyl-thiazolidine-4-carboxylic acid melting at 197°–200°C.; $[\alpha]_D^{20} + 30°$. The splitting of this salt was carried out in a manner analogous to example 1 and resulted in the formation of 19.4 grams (89%) of D-3-formyl-2,2,5,5-tetramethylthiazolidine-4-carboxylic acid melting at 179°–181°C.; $[\alpha]_D^{20} + 54°$. The l-phenyl-propanolamine can be recovered from the mother liquor of the splitting of the salt. After evaporation to dryness of the mother liquor from the splitting of the racemate and treating the residue obtained thereby with isopropyl alcohol there were obtained 35.3 grams (96%) of the salt of L-3-formyl-2,2,5,5-tetramethyl-thiazolidine-4-carboxylic acid and l-phenylpropanolamine which was split in an analogous manner to the diastereomeric salt. There were recovered 20.4 grams (97%) of L-3-formyl-2,2,5,5-tetramethyl-thiazolidine-4-carboxylic acid melting at 179°–180°C.; $[\alpha]_D^{20} - 54°$.

The above is the specification of our parent application with modification to specifically mention that $R_1$ and $R_2$ can be joined together to form an alkylene group, together with illustrative compounds.

It has now been found that it is especially advantageous to add the d,l-phenylpropanolamine (d,l-norephedrine) as a salt rather than as the free base as set forth in the parent case.

d,l-phenylpropanolamine (d,l-norephedrine) is also called d,l-1-phenyl-1-hydroxy-2-aminopropane and is generally produced in the form of its salts. When these salts are subjected directly to racemate splitting there is saved the production of the free base of d,l-phenylpropanolamine.

As salts of d,l-phenylpropanolamine (d,l-norephedrine) there are chiefly employed salts of organic acids, preferably with sulfonic acids and even more preferably with carboxylic acids. As sulfonic acids there can be used for example aliphatic sulfonic acids, e.g. alkane sulfonic acids such as methane sulfonic acid, methane trisulfonic acid, propan-2-sulfonic acid, ethane sulfonic acid, propan-1-sulfonic acid, butan-1-sulfonic acid, decane-1-sulfonic acid, octadecan-1-sulfonic acid; or aromatic sulfonic acids, e.g. aryl sulfonic acids such as p-toluene sulfonic, beta-naphthalene sulfonic acid, alpha-naphthalene sulfonic acid and especially benzene sulfonic acid. As carboxylic acids there can be used saturated or unsaturated aliphatic mono or poly carboxylic acids, in a given case substituted by —OH, $H_2N—$, $NHR—$,

—OR, —SH, —SR or halogen where R for example is an alkyl group. The preferred acids are aliphatic acids having 1 to 6 carbon atoms, especially alkanoic acids having 1 to 6 carbon atoms, most preferably having 1 to 3 carbon atoms. There are also useful araliphatic carboxylic acids, especially phenylalkanoic acids or aromatic carboxylic acids, or heteroaromatic carboxylic acids (i.e. heterocyclic carboxylic acids). Suitable carboxylic acids include isobutyric acid, n-valeric acid, include isobutyric acid, trimethyl acetic acid, lactic acid, oxalic acid, sebacic acid, maleic acid, adipic acid, malonic acid, tartaric acid, succinic acid, fumaric acid, tricarballylic acid, citric acid, crotonic acid, 6-hydroxy hexanoic acid, chloroacetic acid, p-chlorobenzoic acid, bromoacetic acid, fluoroacetic acid, butyric acid, caproic acid, alpha naphthoic acid, beta-chloropropionic acid, methoxyacetic acid, thioglycolic acid, methylmercaptoacetic acid, beta mercaptopropionic acid, acetic acid, propionic acid, formic acid, octanoic acid, phenyl acetic acid, phenyl propionic acid, phenoxyacetic acid, 2,4-dichlorophenoxy acetic acid, 2,4,5-trichlorophenoxyacetic acid, mandelic acid, cinnamic acid, toluic acid, phthalic acid, isophthalic acid, terephthalic acid, 4-chlorophthalic acid, benzoic acid, salicylic acid, thiophene-2-carboxylic acid, thiophene-3-carboxylic acid, thiazole-4-carboxylic acid, furan-2 -carboxylic acid, 2-pyridinecarboxylic acid (picolinic acid), 3-pyridinecarboxylic acid (nicotinic acid), 4-pyridinecarboxylic acid (isonicotinic acid), 3-indoleacetic acid, 2,3-pyridinedicarboxylic acid.

Less preferably there are employed salts of inorganic acids such as sulfuric acid, hydrochloric acid, hydrobromic acid, nitric acid, phosphoric acid.

Preferably there is employed as the optically active thiazolidine-4-carboxylic acid the N-formyl-2,2,5,5-tetramethylthiazolidine-4-carboxylic acid or the N-formyl-2,2-pentamethylene-5,5-dimethylthiazolidine-4-carboxylic acid, especially the D forms of these compounds.

As organic solvents for the reaction employing the salts of d,l-norephedrine there can be used those mentioned above as well as aliphatic hydrocarbons, e.g. decane or heptane. Preferably there are employed benzene or toluene (aromatic hydrocarbons), isopropanol, dioxane and lower alkyl alkanoates, e.g. ethyl acetate. Less preferably there can be used water.

The process of the invention using the salts of d,l-norephedrine is carried out using the same molar proportions as with the free base except that when salts of polybasic acids with norephedrine are employed, it should be noted that 1 mole of ephedrine is available for each acid group, e.g. 1 mole of norephedrine citrate is equivalent to 3 moles of norephedrine.

The recovery of the optically active phenylpropanolamine (norephedrine) and the optically active thiazolidine-4-carboxylic acid of formula I takes place in exactly the same manner as when the free base is employed.

In the following examples the rotatory power of the materials is always given as specific rotation $[\alpha]_D^{20}$ in degrees × cm³/decimeter × grams. Percents are always weight percents.

EXAMPLE 8

To a suspension of 19.7 grams (0.1 mole) of d,l-phenylpropanolamine formate (d,l-norephedrine formate) in 100 ml of n-butyl acetate there were added 21.7 grams (0.1 mole) of D-N-formyl-2,2,5,5-tetramethyl-thiazolidine-4-carboxylic acid at 70°C. The mixture was stirred for 30 minutes at 70° to 90°C and for a further 60 minutes at room temperature. Thereby there separated out the adduct of l-phenylpropanolamine (l-norephedrine) and D-N-formyl-2,2,5,5-tetramethyl-thiazolidine-4-carboxylic acid. The adduct was filtered off, washed with 20 ml of n-butyl acetate and finally dried under reduced pressure at 50°C. It had a specific rotation of +31° and a melting point of 199° to 201°C. The yield was 14.5 grams, corresponding to 79% based on the d,l-phenylpropanolamine formate added.

The adduct recovered was suspended in 50 ml of water and the suspension adjusted to a pH of 1 with concentrated hydrochloric acid at room temperature. In a short time there separated the D-N-formyl-2,2,5,5-tetramethyl-thiazolidine-4-carboxylic acid. This was filtered off with suction and then dried under reduced pressure. There were obtained 7.8 grams of this acid.

The filtrate remaining after the separation of the D-N-formyl-2,2,5,5-tetramethyl-thiazolidine-4-carboxylic acid was adjusted to a pH of 10 with sodium hydroxide and then extracted with methylene chloride. After removal of the extraction agent under reduced pressure, there remained in the extract 5.2 grams of l-phenylpropanolamine, corresponding to a yield of 69% based on the d,l-phenylpropanolamine formate employed. The l-phenylpropanolamine (l-norephedrine) recovered had a specific rotation of −13° and a melting point of 48° to 50°C.

The filtrate remaining after separation of the adduct of l-phenylpropanolamine and D-N-formyl-2,2,5,5-tetramethylthiazolidine-4-carboxylic acid was brought to dryness. There accumulated the adduct of d-phenylpropanolamine (d-norephedrine) and D-N-formyl-2,2,5,5-tetramethyl-thiazolidine-4-carboxylic acid in addition to the diastereomeric adduct of l-phenylpropanolamine l-norephedrine) and D-N-formyl-2,2,5,5,-tetramethyl-thiazolidine-4-carboxylic acid. The mixture was suspended in water and the suspension adjusted to a pH of 1 with hydrochloric acid. D-N-formyl-2,2,5,5-tetramethylthiazolidine-4-carboxylic acid separated out. This was filtered off with suction and then dried under reduced pressure. There were obtained 7 grams of the free thiazolidine-4-carboxylic acid.

The filtrate remaining after the separation of the D-N-formyl-2,2,5,5-tetramethyl-thiazolidine-4-carboxylic acid was adjusted to a pH of 10 with sodium hydroxide and then extracted with methylene chloride. After removal of the extraction agent under reduced pressure, there remained in the extract 6.0 grams of d-phenylpropanolamine (d-norephedrine) corresponding to a yield of 80% based on the d,l-phenylpropanolamine formate added. The d-phenylpropanolamine obtained had a specific rotation of +10° and a melting point of 47 to 50°C., after recrystallization from diisopropyl ether it had a specific rotation of +11.9° and a melting point of 49 to 52°C.

EXAMPLE 9

The procedure of example 8 followed but a solution of 21.7 gram (0.1 mole) of D-N-formyl-2,2,5,5-tetramethylthiazolidine-4-carboxylic acid in 100 ml of ethyl acetate was treated with 21.1 grams (0.1 mole) of d,l-phenylpropanolamine acetate (d,l-norephedrine acetate). First there were recovered 13.8 grams of the adduct of l-phenylpropanolamine and D-N-formyl-2,2,5,5-tetramethyl-thiazolidine-4-carboxylic acid, corresponding to a yield of 75%. The adduct had a specific rotation of +33° and a melting point of 198° to 199°C. Subsequently there were recovered 5.7 grams of l-phenylpropanolamine (l-norephedrine) corresponding to a 76% yield, specific rotation −12.8°, melting point 49° to 51°C., and 5.2 grams of d-phenylpropanolamine (d-norephedrine), corresponding to a 70% yield, specific rotation +12.1°, melting point 50° to 52°C. and also 16.3 grams of D-N-formyl-2,2,5,5-tetramethyl-thiazolidine-4-carboxylic acid.

EXAMPLE 10

The procedure of example 8 was followed but there were reacted 22.5 grams (0.1 mole) of d,l-phenylpropanolamine propionate (d,l-norephedrine propionate) with 21.7 grams (0.1 mole) of D-N-formyl-2,2,5,5-tetramethyl-thiazolidine-4-carboxylic acid. There was recovered 14.7 grams of the adduct of l-phenylpropanolamine and D-N-formyl-2,2,5,5-tetramethyl-thiazolidine-4-carboxylic acid, corresponding to a yield of 80%. The adduct had a specific rotation of +32° and a melting point of 197° to 199°C.

EXAMPLE 11

The procedure of example 8 was followed but there were reacted 30.2 grams (0.1 mole) of d,l-phenylpropanolamine-3-phenylpropionate (d,l-norephedrine-3-phenylpropionate) with 21.7 grams (0.1 mole) of D-N-formyl-2,2,5,5-tetramethyl-thiazolidine-4-carboxylic acid. There were recovered 12.5 grams of the adduct of l-phenylpropanolamine and D-N-formyl-2,2,5,5-tetramethylthiazolidine-4-carboxylic acid, corresponding to a 68% yield. The adduct had a specific rotation of +30° and a melting point of 198° to 200°C.

EXAMPLE 12

The procedure of example 8 was followed but there were reacted 19.7 grams (0.1 mole) of d,l-phenylpropanolamine formate (d,l-norephedrine formate) with 25.7 grams (0.1 mole) of D-N-formyl-2,2-pentamethylene-5,5-dimethyl-thiazolidine-4-carboxylic acid. There were recovered 16.0 grams of the adduct of l-phenylpropanolamine and D-N-formyl-2,2-pentamethylene-5,51 -dimethyl-thiazolidine-4-carboxylic acid. The adduct had a specific rotation of +24.8° and a melting point of 190° to 191°C. There were recovered from the adduct 5.3 grams of l-phenylpropanolamine, corresponding to a yield of 90%. The l-phenylpropanolamine had a specific rotation of −13° and a melting point of 49° to 51°C.

EXAMPLE 13

The procedure of example 8 was followed but there were reacted 20.9 grams (0.05 mole) of d,l-phenylpropanolaminemaleate (d,l-norephedrine maleate) with 25.7 grams (0.1 mole) of D-N-formyl-2,2-pentamethylene-5,5-dimethyl-thiazolidine-4-carboxylic acid. There were recovered 14 grams of the adduct of 1-phenylpropanolamine and D-N-formyl-2,2-pentamethylene-5,5-dimethyl-thiazolidine-4-carboxylic acid, corresponding to a 69% yield. The adduct had a specific rotation of +25.7° and a melting point of 189° to 191°C.

EXAMPLE 14

The procedure of example 1 was followed but there were reacted 30 grams (0.1 mole) of d,l-phenylpropanolaminebenzene sulfonate (d,l-norephedrine benzene sulfonate) with 21.7 grams (0.1 mole) of D-N-formyl-2,2,5,5-tetramethylthiazolidine-4-carboxylic acid. There were recovered 13.7 grams of the adduct of l-phenylpropanolamine and D-N-formyl-2,2,5,5-tetramethyl-thiazolidine-4-carboxylic acid, corresponding to a 75% yield. The adduct had a specific rotation of +33° and a melting point of 198° to 200°C.

What is claimed is:

1. The salt of phenylpropanolamine with a thiazolidine-4-carboxylic acid of the formula

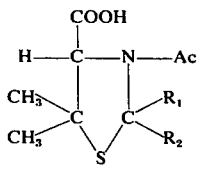

where $R_1$ and $R_2$ together are pentamethylene and Ac is benzoyl, tosyl, nitrophenyl sulfenyl, formyl or acetyl.

2. The salt of claim 1 wherein Ac is formyl or acetyl.

3. The salt of claim 2 wherein Ac is formyl.

4. The salt of an optically active isomer of norephedrine with an optically active form of a thiazolidine carboxylic acid of the formula

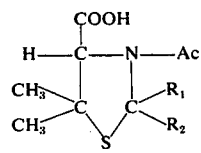

where $R_1$ and $R_2$ together are pentamethylene and Ac is benzoyl, tosyl, nitrophenylsulfenyl, formyl or acetyl.

5. The salt of claim 4 wherein Ac is formyl.

6. The salt of claim 5 which is the salt of l-norephedrine and the D form of the thiazolidine-4-carboxylic acid.

7. The salt of claim 5 which is the salt of d-norephedrine and the L-form of the thiazolidine-4-carboxylic acid.

* * * * *